United States Patent
Tanaka et al.

(10) Patent No.: US 7,592,187 B2
(45) Date of Patent: Sep. 22, 2009

(54) METHOD OF CALIBRATING LIGAND SPECIFICITY

(75) Inventors: Akito Tanaka, Tsukuba (JP); Akira Yamazaki, Suita (JP)

(73) Assignee: Reverse Proteomics Research Institute Co., Ltd. (JP)

( * ) Notice: Subject to any disclaimer, the term of this patent is extended or adjusted under 35 U.S.C. 154(b) by 14 days.

(21) Appl. No.: 10/573,167

(22) PCT Filed: Oct. 15, 2004

(86) PCT No.: PCT/JP2004/015655

§ 371 (c)(1),
(2), (4) Date: Dec. 29, 2006

(87) PCT Pub. No.: WO2005/036174

PCT Pub. Date: Apr. 21, 2005

(65) Prior Publication Data

US 2007/0122913 A1    May 31, 2007

(30) Foreign Application Priority Data

Oct. 15, 2003    (JP)    ............................. 2003-354503

(51) Int. Cl.
*G01N 33/557*    (2006.01)
(52) U.S. Cl. ........................ 436/517; 435/7.1; 436/501; 436/518; 436/524; 436/528; 436/536; 436/537; 436/538; 436/8; 436/34

(58) Field of Classification Search ..................... 435/3, 435/7.1, 7.93, 7.94, 973; 436/501, 517, 518, 436/523–535, 536, 537, 538, 540, 8, 10, 436/16, 34, 164, 174, 175
See application file for complete search history.

(56) References Cited

U.S. PATENT DOCUMENTS

| 4,745,072 | A |   | 5/1988 | Ekins et al. |
| 5,585,241 | A | * | 12/1996 | Lindmo ........................ 435/6 |
| 5,753,518 | A | * | 5/1998 | Karlsson ...................... 436/517 |
| 5,880,177 | A | * | 3/1999 | Higgs et al. .................. 523/217 |

FOREIGN PATENT DOCUMENTS

| JP | 60-501674 A | 10/1985 |
| JP | 9-504859 A | 5/1997 |
| JP | 10-221341 A | 8/1998 |
| JP | 2000-074918 A | 3/2000 |

* cited by examiner

*Primary Examiner*—Gailene R Gabel
(74) *Attorney, Agent, or Firm*—Barnes & Thornburg LLP; Sendil K. Devadas

(57) ABSTRACT

A method to determine specificity of ligand binding includes comparing a solid phase carrier first extract obtained by pretreating a sample with a ligand-immobilized solid phase carrier and a solid phase carrier second extract obtained by treating the pretreated sample again with a ligand-immobilized solid phase carrier in terms of the proteins contained therein, and identifying a protein whose content is remarkably decreased in the second extract compared to the first extract, in order to solve 1) the problem of the solubility of subject ligand, 2) the problem of the non-specific protein-denaturing effect of the subject ligand added, and the like, in antagonism experiments in target search using an affinity resin.

5 Claims, 3 Drawing Sheets

METHOD OF CALIBRATING LIGAND SPECIFICITY

CROSS-REFERENCE TO RELATED APPLICATIONS

This application is a national phase of international patent application no. PCT/JP2004/015655, filed Oct. 15, 2004, which claims the benefit of patent application no. JP 2003-354503, filed Oct. 15, 2003, the entire content of which is incorporated herein by reference.

TECHNICAL FIELD

The present invention relates to analyzing intermolecular interactions using a solid phase carrier. More specifically, the present invention relates to selecting and purifying a molecule exhibiting a specific interaction with a molecule to be analyzed, or to analyze a specific interaction between molecules, by immobilizing the molecule to be analyzed to a solid phase carrier, and measuring and analyzing the intermolecular interaction on the solid phase carrier.

BACKGROUND OF THE INVENTION

In researching target protein interactions using an affinity resin, it is important to determine whether an affinity-bound protein is specific for a ligand or non-specific. Traditionally, to accomplish this purpose, an antagonism experiment that comprises adding a non-modified subject ligand to a starting material protein mixture in advance or simultaneously with the addition of the affinity resin, and confirming the reduction or disappearance of the amount of the subject protein, has been used. Hence, inhibition of the binding of the protein to the affinity resin by the co-presence of the ligand as an antagonist has been considered to be an essential condition for the determination that the protein is specific for the ligand. However, when applying this method, it is often difficult to dissolve a required amount of ligand in the subject protein mixture. This represents representing a drawback in that such experiments are substantially unperformable. In particular, when a pharmaceutical is the subject, which often possesses fat solubility (in particular, orally administrable pharmaceuticals possess fat solubility to ensure membrane permeability by passive diffusion), a sufficient ligand concentration cannot be achieved so that experimental studies of proteins found on affinity resins by antagonism experiments have been abandoned to date. Specifically, to perform an antagonism experiment, it is necessary to dissolve several hundred μg/ml of a ligand (for example, provided that TOYO-Pearl 10 μl=1 μmol is used, in the case of a ligand (antagonist) having a molecular weight of 500, a solubility of not less than 0.5 mg/ml is required, even when an equal amount of drug is present with the ligand on the resin) in an aqueous solution wherein the protein is present; generally, it is difficult to dissolve such a high concentration of ligand in a biological material solution wherein considerable amounts of various ions and solutes such as proteins are dissolved. This limitation is a problem common not only to pharmaceuticals but also to compounds that exhibit interesting pharmacological action in oral administration, for example, environmental substances, toxic substances and the like, and there has been a demand to overcome this limitation in the entire research into drug discovery target search.

Also, in conventional methods, a ligand is often added in an amount not less than the amount of the ligand on the resin to secure an antagonistic effect, and this practice is a major problem of protein denaturation due to the presence of a ligand at a high concentration of several mg/ml in a biological material solution such as a lysate. That is, even if band disappearance due to the addition of a ligand is observed during an antagonism experiment performed to determine the specificity of an affinity-resin-bound protein, it is difficult to determine whether the observation is due to antagonistic effect or derived from the inactivation of the protein by the non-specific protein-denaturing effect of the ligand.

Therefore, there has been a method of determining the ligand specificity of a protein that binds to an affinity resin, which enables solving 1) the problem of the solubility of subject ligand, and 2) the problem of the non-specific protein-denaturing effect of the subject ligand added, which have been problematic in conventional antagonism experiments described above.

It is an object of the present invention to provide a method of determining the ligand specificity of a protein that binds to an affinity resin, particularly to provide a method of determining ligand specificity wherein the solubility of ligand and the non-specific protein-denaturing effect of the added subject ligand are at issue.

BRIEF SUMMARY OF THE INVENTION

In view of the above problems, the present inventors conducted various investigations, and found that by performing a step of "pre-treating with a ligand-immobilized affinity resin" in place of "a step of adding an unmodified ligand directly to a protein mixture" that is performed in antagonism experiments for the conventional method, 1) the problem of the solubility of subject ligand, 2) the problem of the non-specific protein-denaturing effect of the subject ligand added, and the like, can be solved at one time. The present invention establishes a series of methods of determining ligand specificity.

In a sample, particularly in a biological sample, a protein that non-specifically binds and is adsorbed to a particular ligand is present, in addition to a protein that specifically binds to the ligand. Against this background, the present invention relates to a method of determining the ligand specificity of various proteins that bind to a ligand. The present invention is based on the new finding that a protein that specifically binds to a ligand has a high binding constant and preferentially binds to a ligand-immobilized solid phase carrier.

Accordingly, the present invention relates to the following:

[1] A method of determining whether or not the binding of a molecule capable of binding to a ligand to the ligand is specific, which comprises the steps shown below;

(1) a step of treating a sample with a ligand-immobilized solid phase carrier to obtain a treated liquid, and extracting the protein bound onto the solid phase carrier to obtain a ligand-immobilized solid phase carrier first extract, (2) a step of treating the treated liquid obtained in the previous step with a ligand-immobilized solid phase carrier (another solid phase carrier wherein the same kind of ligand as the ligand-immobilized solid phase carrier used in the previous step is immobilized) to obtain a treated liquid, and extracting the protein bound onto the solid phase carrier to obtain a ligand-immobilized solid phase carrier second extract, (3) a step of comparing and analyzing the proteins contained in the ligand-immobilized solid phase carrier first extract and the proteins contained in the ligand-immobilized solid phase carrier second extract, (4) a step of identifying a protein that is detected in the ligand-immobilized solid phase carrier first extract, and that is not detected in the ligand-immobilized solid phase carrier second extract or, even if detected, shows a significantly greater reduction compared to other proteins than in the ligand-immobilized solid phase carrier first extract, on the basis of the analytical results obtained in the step (3), and determining the protein to be specific for the ligand.

[2] The method described in [1] above, which comprises repeating the step (2) twice or more.

[3] A method of determining whether or not the binding of a molecule capable of binding to a ligand to the ligand is specific, which comprises the steps shown below;

(1) a step of dividing a sample into two portions, and treating one thereof with an inert-substance-immobilized solid phase carrier to obtain a treated liquid, (2) a step of treating the treated liquid after treatment with the inert-substance-immobilized solid phase carrier, obtained in the previous step, with a ligand-immobilized solid phase carrier (another solid phase carrier wherein the same kind of ligand as the ligand-immobilized solid phase carrier used in the step (3) and step (4) described below is immobilized) to obtain a treated liquid, and extracting the protein bound onto the solid phase carrier to obtain a ligand-immobilized solid phase carrier first extract, (3) a step of treating the remaining portion of the sample divided into two portions in the step (1) with a ligand-immobilized solid phase carrier to obtain a treated liquid, (4) a step of treating the treated liquid after treatment with the ligand-immobilized solid phase carrier, obtained in the previous step, with a ligand-immobilized solid phase carrier (another solid phase carrier wherein the same kind of ligand as the ligand-immobilized solid phase carrier used in the previous step (3) is immobilized) to obtain a treated liquid, and extracting the protein bound onto the solid phase carrier to obtain a ligand-immobilized solid phase carrier second extract, (5) a step of comparing and analyzing the proteins contained in the ligand-immobilized solid phase carrier first extract and the proteins contained in the ligand-immobilized solid phase carrier second extract, (6) a step of identifying a protein that is detected in the ligand-immobilized solid phase carrier first extract, and that is not detected in the ligand-immobilized solid phase carrier second extract or, even if detected, shows a significantly greater reduction compared to other proteins than in the ligand-immobilized solid phase carrier first extract, on the basis of the analytical results obtained in the step (5), and determining the protein to be specific for the ligand.

[4] The method described in [3] above, wherein the inert substance is stearic acid.

[5] The method described in [3] above, wherein the inert substance is structurally similar to the subject ligand, and does not possess the physiological activity possessed by the ligand.

[6] The method described in [1] or [3] above, wherein the sample is a biological sample.

[7] The method described in [1] or [3] above, which further comprises a step of calculating the binding constant of the protein in the sample to the ligand by comparison and analysis.

DETAILED DESCRIPTION OF THE INVENTION

Figure 1:
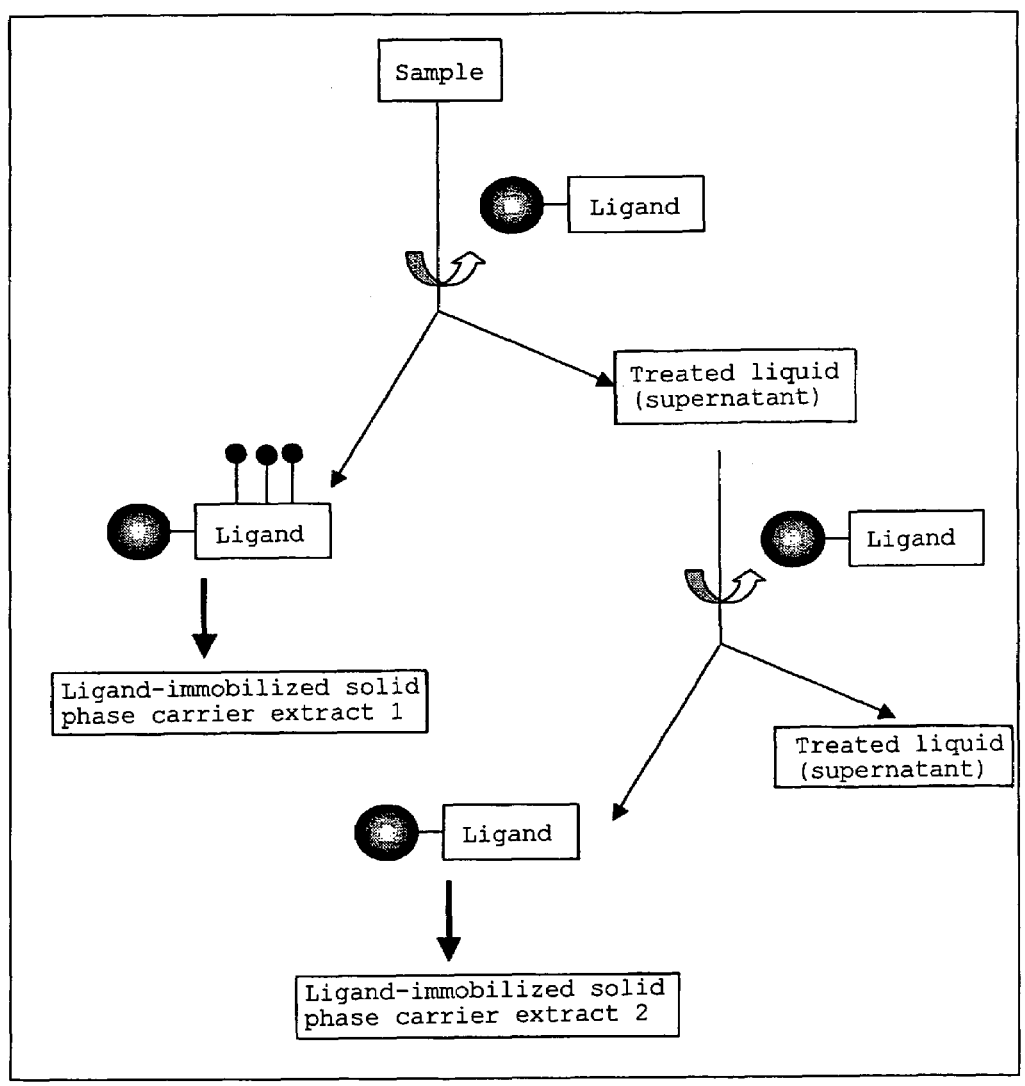
FIG. 1 is a drawing schematically showing a mode of an embodiment of the present invention.

A mode of an embodiment of the present invention is schematically shown in FIG. 1 (mode of embodiment 1). (1) A step of treating a sample with a ligand-immobilized solid phase carrier to obtain a treated liquid, and extracting the protein bound onto the solid phase carrier to obtain a ligand-immobilized solid phase carrier first extract.

The sample used in this step can comprise a substance that specifically binds to the subject ligand, and comprises a plurality of substances. The sample may consist essentially of known compounds, may comprise some novel compounds, and may consist essentially of novel compounds. In a sample consisting essentially of known compounds, a mixture of purified proteins prepared by gene engineering using *Escherichia coli* and the like, are included. A sample comprising some novel compounds include a biological sample such as blood, plasma, serum, urine, or a cell or tissue extract or lysate. In a sample consisting essentially of novel compounds, a mixture of novel proteins whose functions and structures are not yet known, or newly synthesized compounds and the like are included. When the sample is a mixture, especially when it comprises known compounds, the contents of these compounds in the sample may optionally be set at desired levels in advance, but need not always be determined.

Specificity of various substances such as proteins, nucleic acids, sugars, and lipids can be determined. The proteins encompass complex proteins such as glycoproteins and lipoproteins, as well as simple proteins.

Depending on sample derivation and properties, in the method of solid phase carrier treatment described below and the like, the sample can be diluted with an appropriate buffer solution as required. The buffer solution includes but are not limited to the ones that do not adversely affect the specific interaction between the ligand and the target molecule. For example, physiological saline, phosphate buffer solution, tris-HCl buffer solution and the like are suitable, and a stabilizer, an antiseptic and the like may be added if desired.

In the present invention, the ligand to be immobilized to the solid phase carrier is not includes but is not limited to a known compound or a novel compound that will be developed in the future. Also, the ligand may be a low-molecular compound or a high-molecular compound. Here, a low-molecular compound refers to a compound having a molecular weight of less than about 1000; for example, an organic compound commonly usable as a pharmaceutical, a derivative thereof, and an inorganic compound are suitable. Specifically, a compound produced by a method of organic synthesis and the like, a derivative thereof, a naturally occurring compound, a derivative thereof, a small nucleic acid molecule such as a promoter, various metals, and the like are suitable. Desirably, an organic compound that can be used as a pharmaceutical, a derivative thereof, or a nucleic acid molecule is suitable. Also, in addition to the high-molecular compound, a compound having a molecular weight of not less than about 1000, e.g., a protein, a polynucleic acid, a polysaccharide, or a combination thereof, and the like are suitable. A protein is desirable. These low-molecular compounds or high-molecular compounds are commercially available if they are known compounds, or can be obtained via steps such as of collection, production and purification according to various publications. These may be of natural origin, or may be prepared by genetic engineering, or may be obtained by semi-synthesis and the like.

Immobilization of a ligand to a solid phase carrier can be performed in accordance with a method commonly performed in the art. As a convenient and reliable means, a method utilizing an amide bond formation reaction can be mentioned. This reaction can, for example, be performed according to "Peputido Gousei no Kiso to Jikken" (ISBN 4-621-02962-2, Maruzen, 1st edition issued in 1985). Regarding the reagents and solvents used in each reaction, those in common use in the art can be utilized, and are selected appropriately depending on the binding reaction employed.

The solid phase carrier used in the present invention includes but is not limited to carriers that allow a specific interaction between the ligand and the target molecule and those commonly used in the art can be utilized, and the solid phase carrier is chosen appropriately depending on the methods performed to treat the sample and prepare a ligand-immobilized solid phase carrier extract. As examples of the material, resins (polystyrene, methacrylate resins, polyacrylamide and the like), glass, metals (gold, silver, iron, silicon and the like) and the like can be used. These solid phases may be of any form, and are chosen appropriately depending on the kind of the above-described material and the method performed for treating the sample and preparing a ligand-immobilized solid phase carrier extract. For example, plates, beads, thin films, threads, coils and the like can be used.

Treatment of a sample with a ligand-immobilized solid phase carrier is conveniently performed by mixing the ligand-immobilized solid phase carrier and the sample. For example, a bead-like ligand-immobilized solid phase carrier is mixed with a sample (preferably liquid) at 4° C. to room temperature with gentle stirring for 30 minutes to overnight. When the sample is not liquid, it is preferably dissolved in an appropriate buffer solution and the like to make it liquid in advance as described above. After the treatment, the ligand-immobilized solid phase carrier and the sample are separated. This means of separation is also set forth appropriately depending on the form and material of the ligand-immobilized solid phase carrier and the like; for example, when a bead-like solid phase carrier is used, separation by centrifugal operation or filtration is suitable. With respect to the conditions of centrifugal operation, various conditions commonly performed in the art are employed. Specifically, centrifugal operation at 4° C. to room temperature and 100 to 15000 g for 1 second to 10 minutes and filtration using a membrane of meshes that do not allow the passage of the solid phase carrier can be used. The supernatant or filtrate and the like obtained through these operations is referred to as a treated liquid.

While obtaining a treated liquid as described above, the protein bound onto the solid phase carrier is extracted from the precipitate or residue obtained by centrifugal operation or filtration of the ligand-immobilized solid phase carrier, to yield a ligand-immobilized solid phase carrier extract. The ligand-immobilized solid phase carrier extract obtained by first treating the sample with the ligand-immobilized solid phase carrier is referred to as "ligand-immobilized solid phase carrier first extract" for convenience.

With respect to the method of extracting the protein bound onto the ligand-immobilized solid phase carrier, various methods commonly performed in the art can be utilized. This extraction is performed by, for example, treating the ligand-immobilized solid phase carrier with a surfactant-containing extract. Sodium dodecyl sulfate (SDS), polyoxyethylene sorbitan monolaurate (for example, trade name: Tween 20), polyoxyethylene(9)octylphenyl ether (for example, trade name NP-40) and the like can be used as surfactants. As described below, when using SDS-PAGE for protein detection, it is suitable to directly extract the protein with an SDS-containing sample buffer for SDS-PAGE.

(2) The treated liquid obtained in the previous step (step (1)) is treated with a ligand-immobilized solid phase carrier to obtain a treated liquid, and the protein bound onto the solid phase carrier is extracted to obtain a ligand-immobilized solid phase carrier second extract.

The ligand-immobilized solid phase carrier used in this step is another solid phase carrier wherein the same kind of ligand as the ligand-immobilized solid phase carrier used in the previous step (step (1)) is immobilized.

Treatment of the treated liquid with the ligand-immobilized solid phase carrier is performed in the same manner as the treatment of the sample with the ligand-immobilized solid phase carrier performed in the step (1), and is conveniently performed by mixing the ligand-immobilized solid phase carrier and the treated liquid. For example, a bead-like ligand-immobilized solid phase carrier is mixed with the treated liquid at 4° C. to room temperature with gentle stirring for 30 minutes to overnight. After the treatment, the ligand-immobilized solid phase carrier and the treated liquid are separated. This means of separation is also set forth appropriately depending on the form and material of the ligand-immobilized solid phase carrier and the like. For example, when a bead-like solid phase carrier is used, separation by centrifugal operation or filtration is suitable. With respect to the conditions of centrifugal operation, various conditions commonly performed in the art are employed. Specifically, centrifugal operation at 4° C. to room temperature and 100 to 15000 g for 1 second to 10 minutes and filtration operation using a membrane of meshes that do not allow the passage of the solid phase carrier can be performed.

From the precipitate or residue obtained by centrifugal operation or filtration operation, that is, a ligand-immobilized solid phase carrier, the protein bound onto the solid phase carrier is extracted to yield a ligand-immobilized solid phase carrier extract. A ligand-immobilized solid phase carrier extract obtained by treating the treated liquid with the ligand-immobilized solid phase carrier is referred to as "ligand-immobilized solid phase carrier second extract" for convenience. When this step is repeated twice or more, a plurality of portions of ligand-immobilized solid phase carrier second extract are obtained depending on the number of repeats. To prevent confusion in such cases, the portions may be distinguished from each other by designating as ligand-immobilized solid phase carrier extract 2a, 2b, 2c . . . and the like.

The method of extracting the protein bound onto the ligand-immobilized solid phase carrier in this step is the same as the method performed in the previous step (step (1)).

(3) A step of comparing and analyzing the proteins contained in the ligand-immobilized solid phase carrier first extract and the proteins contained in the ligand-immobilized solid phase carrier second extract.

This step can employ an ordinary method of protein analysis. For example, analysis by SDS-PAGE is convenient. By subjecting the ligand-immobilized solid phase carrier first extract and the ligand-immobilized solid phase carrier second extract to SDS-PAGE under the same conditions, and comparing the electrophoretic patterns obtained, protein differences in the individual extracts can be examined.

4) A protein that is detected in the ligand-immobilized solid phase carrier first extract, and that is not detected in the ligand-immobilized solid phase carrier second extract or, even if detected, shows a significantly greater reduction compared to other proteins than in the ligand-immobilized solid phase carrier first extract, on the basis of the analytical results obtained in the step (3), is determined to be specific for the ligand.

This step is based on the finding obtained in the invention of this application that proteins of higher specificity (proteins having higher binding constants) are more likely to be lost from the sample (or treated liquid) during the first ligand-immobilized solid phase carrier treatment. To "show a significantly greater reduction compared to other proteins than in the ligand-immobilized solid phase carrier first extract" is visually determinable, and can be determined by a statistical process commonly performed in the art (for example, a comparison of overall protein content changes and the reduction rate of the content of a particular protein).

Figure 2:
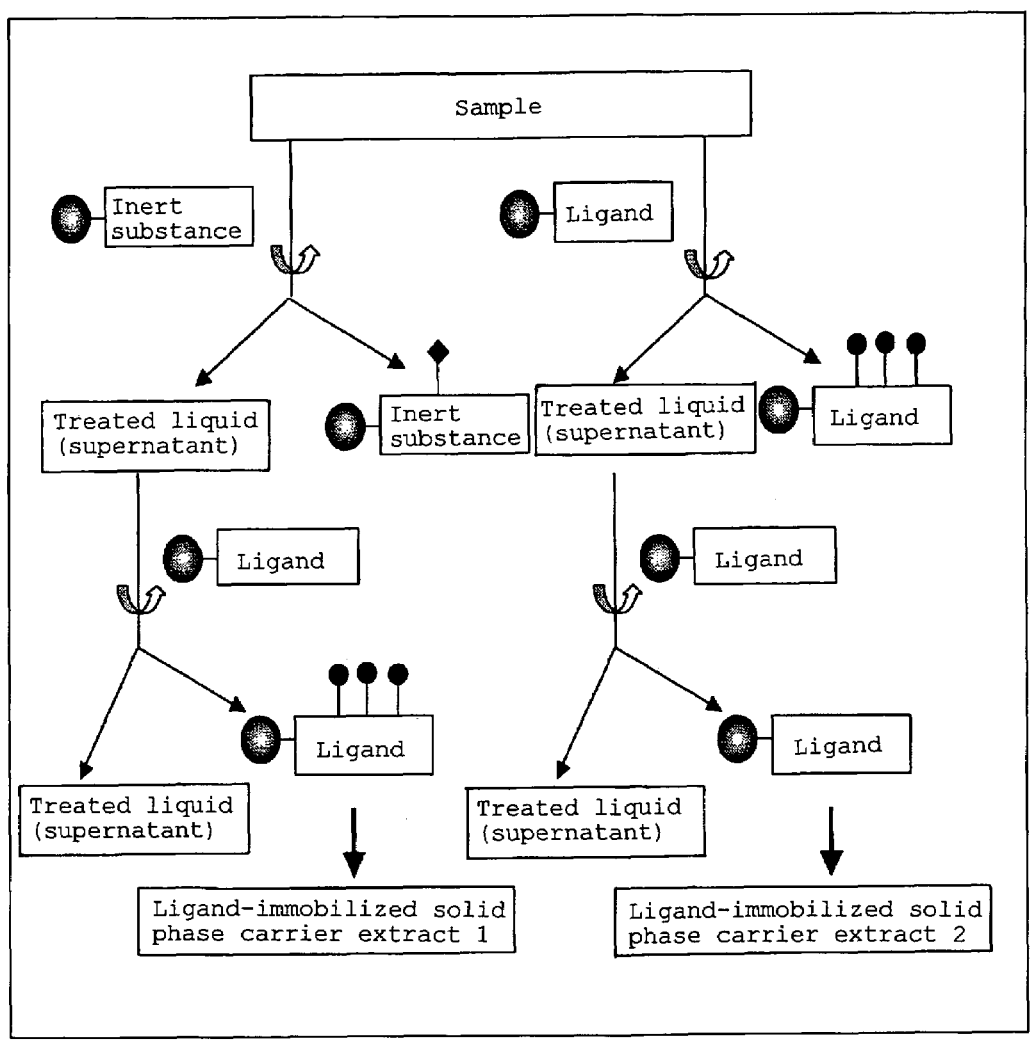
FIG. 2 is a drawing schematically showing a mode of an embodiment of the present invention.

Furthermore, another mode of embodiment of the present invention is shown in FIG. 2. This mode of embodiment comprises a step of treating with a solid phase carrier wherein an inert substance is immobilized. This mode of embodiment is described below (mode of embodiment 2).

(1) A sample is divided into two portions, and treating one thereof with an inert-substance-immobilized solid phase carrier to obtain a treated liquid.

The sample used in this step is the same as described above. The sample is divided into two portions in advance, one of which is used in this step, and the remaining portion is used in step (3) described below. For comparison and analysis in the step (5), the portions of sample serving as the starting materials for the step (1) and the step (3) need to be identical (that is, having the same composition), and the sample is therefore preferably divided into two portions in advance. If the ligand-specific molecule is capable of binding onto the ligand-immobilized solid phase carrier, the sample may be divided into two equal amounts of portions, and may be divided into two mutually different amounts of portions.

The inert substance immobilized onto a solid phase carrier in the present invention includes, for example, a substance other than the ligand for which a target molecule is searched, and is a substance that does not possess the physiological activity possessed by the ligand. Because the inert substance is expected to exhibit nearly the same behavior as the ligand with regard to non-specific protein adsorption, the inert substance is more preferably a substance similar to the ligand in terms of characteristic functional group and core. For example, provided that the ligand for which a target molecule is searched is a substance exhibiting anti-inflammatory effect, the inert substance is a substance that does not exhibit anti-inflammatory effect, preferably a structurally similar substance with similar physicochemical properties. If the information on the structure-activity relationship of the ligand is available in advance and utilizable, it is possible to select an inert substance appropriately according to the information, and prepare a solid phase carrier wherein the inert substance is immobilized. Meanwhile, if no such information is available in advance, a hydrophobic substance that is expected to normally produce non-specific protein adsorption may be immobilized. As an example of a hydrophobic substance, stearic acid and the like can be used. Degree of hydrophobicity can generally be expressed by a hydrophobicity parameter; in the present invention, the hydrophobicity of "hydrophobic substance" can be defined by a partition coefficient, specifically LOGP. In calculating LOGP, CLOGP (a predicted value obtained using a software program for estimating a hydrophobicity parameter of a compound by a computer can be calculated using, for example, Corwin/Leo's program (CLOGP, Daylight Chemical Information System Co., Ltd.)) and the like are conveniently utilized, but the hydrophobicity parameter is not limited to CLOGP. The greater the CLOGP, the higher the hydrophobicity is. In removing non-specific substances, the LOGP of the hydrophobic substance of the present invention is 4 or more, preferably 6 or more, calculated as CLOGP. If the LOGP is less than 4, no sufficient non-specific substance removal effect is obtained. Also, the greater the LOGP, the higher the hydrophobicity is, although a substance possessing such high hydrophobicity is suitable for achieving an object of the present invention, wherein the effect thereof does not increase remarkably even if it exceeds about 20, calculated as CLOGP. From the viewpoint of the ease of synthesis, the CLOGP is normally not more than 20. Also, because the problem resides in the non-specific interactions based on hydrophobic interactions on the solid phase carrier, degree of the hydrophobicity of "hydrophobic substance" may be defined more strictly as the hydrophobicity in a state immobilized on the solid phase carrier, that is, for the entire hydrophobic-substance-immobilized solid phase carrier.

The hydrophobic substance used in the present invention is not limited, as long as it possesses the above-described properties; such as for example, it has an LOGP of 4 or more, preferably 6 or more, calculated as CLOGP. More specifically, the hydrophobic substance is at least selected from the group consisting of undecanoic acid, myristic acid, palmitic acid, linoleic acid, arachidonic acid, linolenic acid, oleic acid, stearic acid, 9-(naphthalen-1-yl)-nonanic acid, dodecanesulfonic acid, octadecanesulfonic acid and hexadecanesulfonic acid, preferably at least one selected from the group consisting of myristic acid, palmitic acid, linoleic acid, arachidonic acid, linolenic acid, oleic acid, stearic acid, octadecanesulfonic acid and hexadecanesulfonic acid, and particularly preferably stearic acid or octadecanesulfonic acid.

The above-described "hydrophobic substance" is commercially available if it is a known substance, or can be prepared according to various publications. If the "hydrophobic substance" is a novel substance, it can be prepared appropriately by utilizing various reactions in organic synthesis commonly performed in the art.

The "inert substance" used in the present invention is also commercially available if it is a known substance, or can be prepared according to various publications. If the "inert substance" is a novel substance, it can be prepared appropriately by utilizing various reactions in organic synthesis commonly performed in the art. In the case of a novel substance, it is confirmed in advance not to possess the desired physiological activity, and preferably to be structurally similar to the test subject ligand and have similar physicochemical properties.

With respect to the solid phase carrier for immobilizing an "inert substance" such as a hydrophobic substance, those available in the art can be used suitably. As examples of the material, resins (polystyrene, methacrylate resins, polyacrylamide and the like), glass, metals (gold, silver, iron, silicon and the like) and the like can be used. These solid phase carriers may be of any form, and are chosen appropriately depending on the kind of the above-described material and the method later performed to analyze intermolecular specific interactions. For example, plates, beads, thin films, threads, coils and the like can be used; beads consisting of a resin that simplify the subsequent operation when packed in a column are suitable, and metallic thin films and glass plates are also suitable.

Immobilization of an inert substance to the solid phase carrier is performed by known methods commonly performed in the art and appropriate combinations thereof. For example, immobilization by covalent bonds or non-covalent bonds such as amide bonds, Schiff base formation, C—C bonds, ester bonds, hydrogen bonds, and hydrophobic interactions can be performed. All these are performed using materials and reactions known in the art. Each binding is performed by utilizing a reaction commonly performed in the art. As a convenient and reliable means, a method utilizing an amide bond formation reaction can be mentioned. This reaction can, for example, be performed according to "Peputido Gousei no Kiso to Jikken" (ISBN 4-621-02962-2, Maruzen, 1st edition issued in 1985). Regarding the reagents and solvents used in each reaction, those in common use in the relevant field can be utilized, and are chosen appropriately depending on the binding reaction employed. Whether or not the hydrophobic substance has been immobilized to the solid phase carrier can, for example, be confirmed from the reaction rate determined by a quantification (for example, the ninhydrin test) of amino groups on the solid phase carrier surface before and after the reaction.

Treatment of a sample with an inert-substance-immobilized solid phase carrier is conveniently performed by mixing the inert-substance-immobilized solid phase carrier and the sample. For example, a bead-like inert-substance-immobilized solid phase carrier is mixed with a sample (preferably liquid) at 4° C. to room temperature with gentle stirring for 30 minutes to overnight. When the sample is not liquid, it is preferably dissolved in an appropriate buffer solution and the like to make it liquid in advance as described above. After the treatment, the inert-substance-immobilized solid phase carrier and the sample are separated. This means of separation is also set forth appropriately depending on the form and material of the inert-substance-immobilized solid phase carrier and the like. For example, when a bead-like solid phase carrier is used, separation by centrifugal operation or filtration is suitable. With respect to the conditions of centrifugal operation, various conditions commonly performed in the art are employed. Specifically, centrifugal operation at 4° C. to room temperature and 100 to 15000 g for 1 second to 10 minutes and filtration operation using a membrane of meshes that do not allow the passage of the solid phase carrier can be performed. The supernatant or filtrate obtained through these treatments is referred to as a treated liquid. Note that although the method and procedures for the above-described treatment can be performed appropriately as described above, it is preferable, from the viewpoint of comparison, that they be performed under the same conditions using the same method and procedures as the treatment of ligand-immobilized solid phase carrier and sample (or treated liquid) described below.

(2) The treated liquid after treatment with the inert-substance-immobilized solid phase carrier, obtained in the previous step (step (1)), is treated with a ligand-immobilized solid phase carrier to obtain a treated liquid, and the protein bound onto the solid phase carrier is extracted to obtain a ligand-immobilized solid phase carrier first extract.

The ligand-immobilized solid phase carrier used in this step is another solid phase carrier wherein the same kind of ligand as the ligand-immobilized solid phase carrier used in the steps described below (step (3) and step (4)) is immobilized.

Treatment of the treated liquid with a ligand-immobilized solid phase carrier can be performed in the same manner as the treatment of the sample with the inert-substance-immobilized solid phase carrier performed in the step (1). After the treatment, the protein bound onto the solid phase carrier is extracted to yield a ligand-immobilized solid phase carrier first extract. This procedure can also be performed using the same conditions and procedures as those described in detail in the mode of an embodiment 1.

(3) A step of treating the sample with a ligand-immobilized solid phase carrier yields a treated liquid.

The sample used in this step is the remaining portion of the sample divided into two portions in the step (1) above.

The ligand-immobilized solid phase carrier used in this step is another solid phase carrier wherein the same kind of ligand as the ligand-immobilized solid phase carrier used in the step (2) is immobilized, and can be prepared in the same manner as the "ligand-immobilized solid phase carrier" described in detail in the mode of embodiment 1. Also, treatment of the sample with the ligand-immobilized solid phase carrier and recovery of the treated liquid can also be performed in the same manner as the treatment performed in the above-described mode of embodiment 1.

(4) The treated liquid after treatment with the ligand-immobilized solid phase carrier, obtained in the previous step (step (3)), is treated with a ligand-immobilized solid phase carrier (another solid phase carrier wherein the same kind of ligand as the ligand-immobilized solid phase carrier used in the previous step (3) is immobilized) to obtain a treated liquid, and the protein bound onto the solid phase carrier is extracted to obtain a ligand-immobilized solid phase carrier second extract.

A series of operations such as treatment of the treated liquid with the ligand-immobilized solid phase carrier, recovery of the treated liquid and extraction of the protein bound to the solid phase carrier to yield a ligand-immobilized solid phase carrier second extract, are performed in accordance with the above-described mode of embodiment 1.

(5) A step of comparing and analyzing the proteins contained in the ligand-immobilized solid phase carrier first extract and the proteins contained in the ligand-immobilized solid phase carrier second extract is performed.

This step can employ an ordinary method of protein analysis. For example, analysis by SDS-PAGE is convenient. By subjecting the ligand-immobilized solid phase carrier extract 1 and the ligand-immobilized solid phase carrier extract 2 to SDS-PAGE under the same conditions, and comparing the electrophoretic patterns obtained, protein differences in the individual extracts can be examined.

(6) A protein that is detected in the ligand-immobilized solid phase carrier extract 1, and that is not detected in the ligand-immobilized solid phase carrier extract 2 or, even if detected, shows a significantly greater reduction compared to other proteins than in the ligand-immobilized solid phase carrier extract 1, on the basis of the analytical results obtained in the step (5), is determined to be specific for the ligand.

This step, as in the mode of embodiment 1, is based on the finding obtained in the invention of this application that proteins of higher specificity (proteins having higher binding constants) are more likely to be removed from the sample (or treated liquid) during the first ligand-immobilized solid phase carrier treatment. That is, even when the sample is treated with an inert-substance-immobilized solid phase carrier in advance, the ligand-specific protein is not removed from the sample. To the contrary, the ratio of ligand-specific protein in the sample increases (the non-specific proteins in the sample are removed by treatment with inert-substance-immobilized solid phase carrier). Meanwhile, when pretreatment with an inert-substance-immobilized solid phase carrier is not performed, as is evident from the mode of embodiment 1, the first ligand-immobilized solid phase carrier treatment causes the ligand-specific protein to be removed from the sample (that is, the ligand-specific protein binds to the immobilized solid phase carrier used for the treatment, hence the ligand-specific protein is contained at high concentrations in the ligand-immobilized solid phase carrier extract obtained after the first ligand-immobilized solid phase carrier treatment).

To "show a significantly greater reduction compared to other proteins than in the ligand-immobilized solid phase carrier extract 1" is visually determinable, and can be determined by a statistical process commonly performed in the art (for example, a comparison of overall protein content changes and the reduction rate of the content of a particular protein).

When a more quantitative determination is required in determining whether or not a particular protein is ligand-specific using the method of the present invention, a step of calculating the binding constant of the protein to the ligand may be included in the above-described series of steps.

For a method of calculating the binding constant, a method commonly performed in the art can be used. For example, ELISA experiments using a labeled ligand, experiments using BIACORE (see Analytical Chemistry (1999), 71, 777-790 by Whiteside et al. and the like) and the like, and the like can be performed.

EXAMPLES

The present invention is hereinafter described in more detail by the following examples, which, however, are not to be construed as limiting the scope of the present invention. Also, the individual compounds, reagents and the like used are commercially available or can be prepared on the basis of published reports and the like unless otherwise stated.

Preparation of Ligand-Immobilized Solid Phase Carrier

Production Example 1

Synthesis of 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-diox-4-aza-tricyclo [22.3.1.0$^{4,9}$]octacos-18-ene-2,3,10,16-tetraone

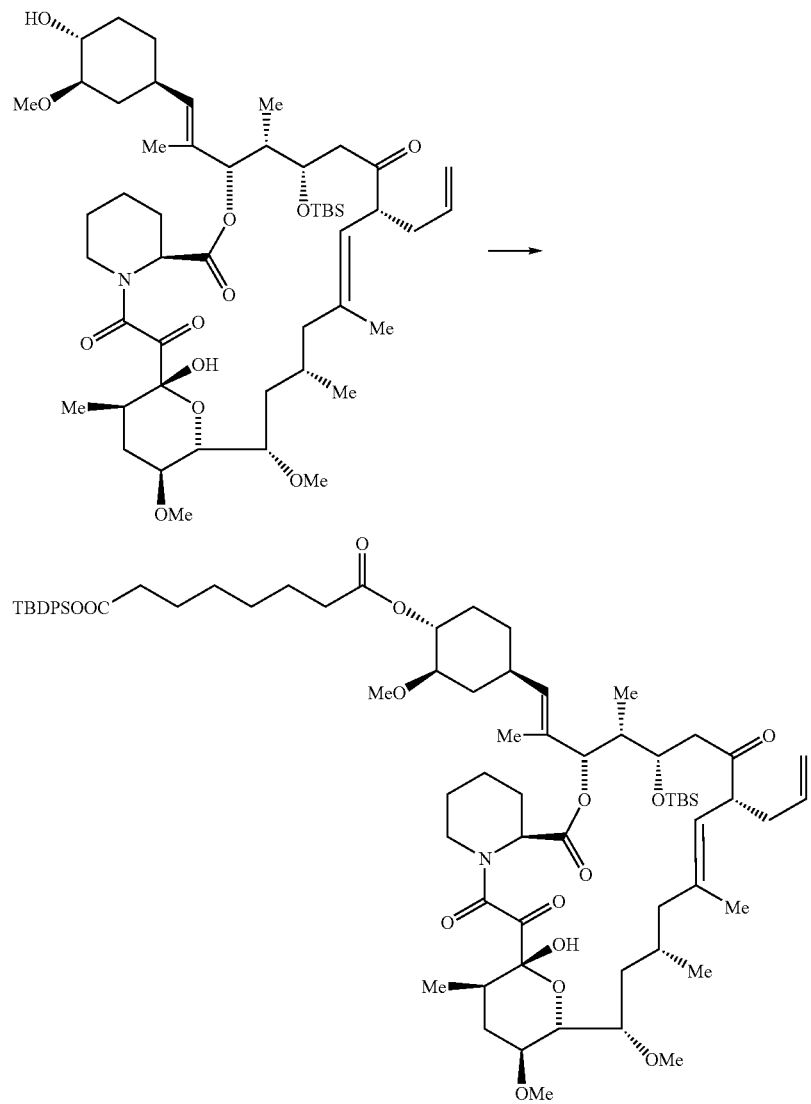

A mixture of 17-allyl-14-(tert-butyl-dimethyl-silanyloxy)-1-hydroxy-12-[2-(4-hydroxy-3-methoxy-cyclohexyl)-1-methyl-vinyl]-23,25-dimethoxy-13,19,21,27-tetramethyl-11,28-diox-4-aza-tricyclo[22.3.1.0$^{4,9}$]octacos-18-ene-2,3,10,16-tetraone (FK506; 138 mg, 0.15 mmol), O-mono(tert-butyl-dimethyl-silanyl)octanedioic acid (86.7 mg, 0.218 mmol), dimethylaminopyridine (DMAP; 16.5 mg, 0.098 mmol), 1-[3-(dimethylamino)propyl]-3-ethylcarbodiimide hydrochloride (EDC/HCl; 69.1 mg, 0.261 mmol) and methylene chloride (CH$_2$Cl$_2$; 1 ml) was stirred at room temperature for 1.5 hours. The reaction product was poured over an ethyl acetate-water mixed liquid and extracted. The organic phase obtained was washed with water and saline, after which it was dried with magnesium sulfate (MgSO$_4$). After the MgSO$_4$ was separated by filtration, concentration under reduced pressure was conducted. The residue thus obtained was purified using a silica gel column (eluted with 20% AcOEt (in n-hexane)) to yield the desired 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone (44 mg, 24.6%).

$^1$H-NMR (CDCl$_3$) δ: −0.1-0.1 (12H, m), 0.7-2.6 (47H, m), 0.85 and 0.86 (18H, s), 1.50 (3H, s), 1.63 (3H, s), 2.75 (1H, m), 3.31 (3H, s), 3.35 (3H, s), 3.39 (3H, s), 4.05 (1H, m), 3.0-4.4 (6H), 4.5-5.8 (9H, m).

Production Example 2

Synthesis of 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone

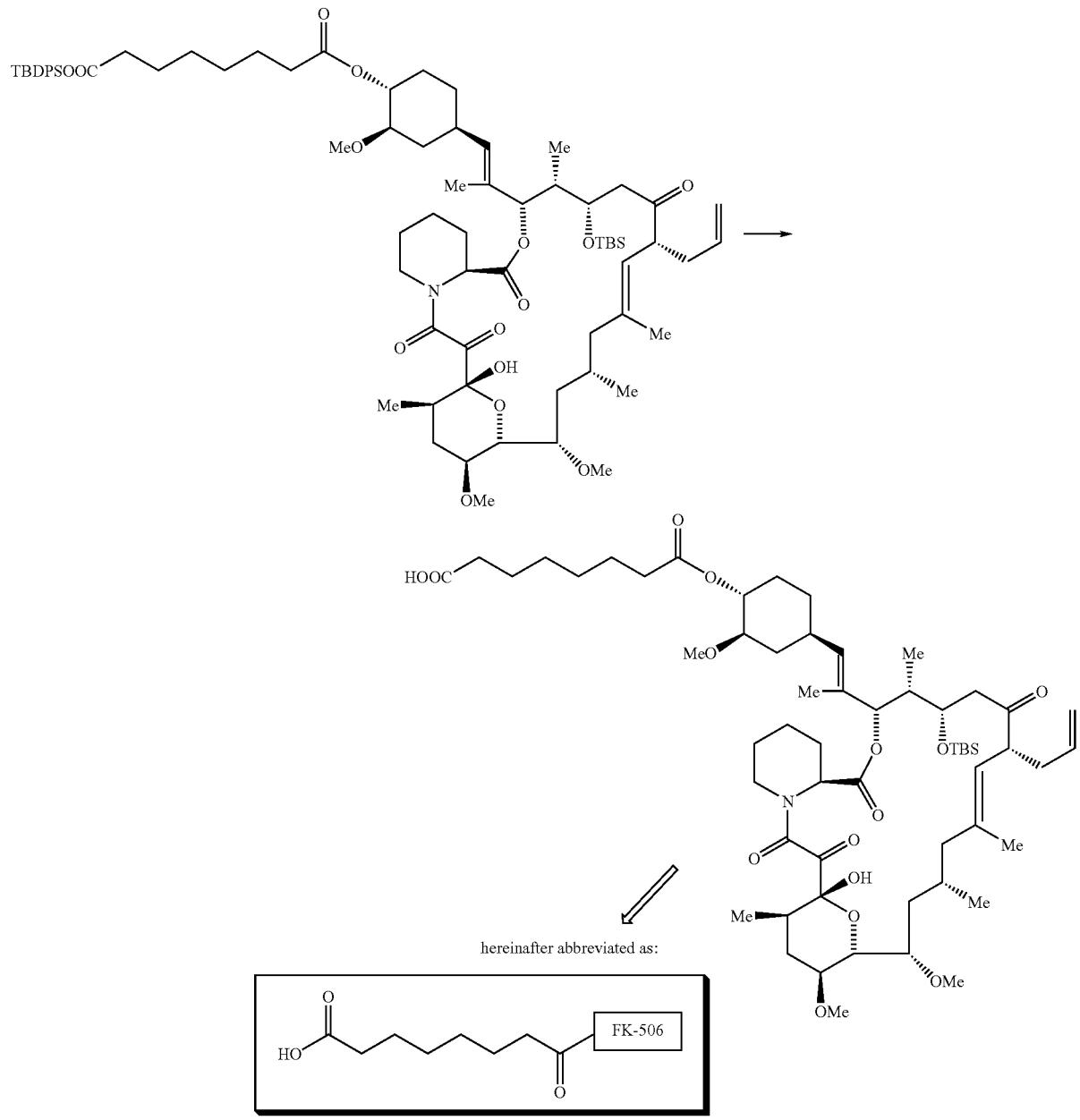

hereinafter abbreviated as:

To a mixture of the 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Production Example 1 (44 mg, 0.037 mmol) and acetonitrile (0.88 ml), 46 to 48% aqueous hydrogen fluoride (HF) (0.12 ml) was gently added; this was followed by overnight stirring at room temperature. The reaction product was poured over an ethyl acetate-water mixed liquid and extracted. The organic phase obtained was washed with water and saline, after which it was dried with magnesium sulfate (MgSO$_4$). After the MgSO$_4$ was separated by filtration, concentration under reduced pressure was conducted. The residue thus obtained was purified using a silica gel column (5% methanol (in chloroform)) to yield the desired 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (14.2 mg, 40%).

$^1$H-NMR (CDCl$_3$) δ: 0.7-2.6 (47H, m), 1.50 (3H, s), 1.63 (3H, s), 2.75 (1H, m), 3.31 (3H, s), 3.35 (3H, s), 3.39 (3H, s), 4.05 (1H, m), 3.0-4.4 (6H), 4.5-5.8 (11H, m). MS (m/z): 960 (M$^+$)

Production Example 3

Synthesis of FK506-Bound TOYO-Pearl Resin

TOYO-Pearl Resin; TSKgel AF-Amino

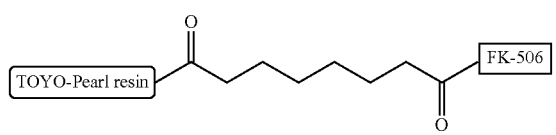

A mixture of the 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Production Example 2 (38.4 mg, 0.04 mmol), TOYO-Pearl resin (TSKgel AF-amino, 100 μl, free amino group (available amino group) content 0.01 mmol; manufactured by Tosoh Corporation), EDC/HCl (9.2 mg, 0.048 mmol), 1-hydroxybenzotriazole (HOBt; 6.5 mg, 0.048 mmol) and dimethylformamide (DMF; 1 ml) was stirred at room temperature for 6 hours. The reaction end point was confirmed when no residual amino groups became visually observable by the ninhydrin reaction. The reaction rate was calculated to be about 24% (estimated ligand concentration=24 μmol/ml). After confirmation of completion of the reaction, the resin was washed with DMF five times. Acetic anhydride (100 μl) and DMF (400 μl) were added thereto, and this was followed by stirring at room temperature for 1 hour. Subsequently, the resin was thoroughly washed with DMF, and the FK506-bound TOYO-Pearl resin obtained was used in the binding experiments described below.

Preparation of Hydrophobic-Substance-Immobilized Solid Phase Carrier

Production Example 4

Synthesis of Stearic-Acid-Immobilized Resin [TOYO+Stearic Acid]

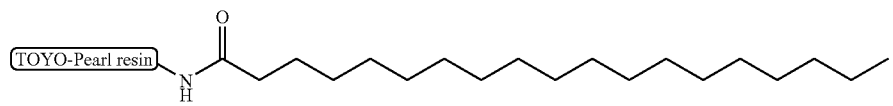

Stearic acid was immobilized to TOYO-Pearl resin (TSK-gel AF-amino). To 100 μl of the TOYO-Pearl resin, stearic acid (11.38 mg, 0.04 mmol) dissolved in a mixed solvent of DMF (0.25 ml) and dichloromethane (0.25 ml) was added; benzotriazol-1-yl-oxy-tris-pyrrolidino-phosphonium hexafluorophosphate (PyBOP; 26 mg, 0.05 mmol) and N,N-diisopropylethylamine (17 μl, 0.10 mmol) were further added, and this was followed by shaking at room temperature for 4 hours. After completion of the reaction, the resin was thoroughly washed with DMF, after which the percent condensation yield was determined by the ninhydrin test (about 91%).

Example 1

(1-1) Preparation of Lysate

The rat brain (2.2 g) was mixed in a mixture A (0.25 M sucrose, 25 mM Tris buffer (pH 7.4), 22 ml) and prepared as a homogenate, which was then centrifuged at 9500 rpm for 10 minutes. The centrifugal supernatant was collected and further centrifuged at 50000 rpm for 30 minutes. The supernatant thus obtained was used as the lysate. Note that all experiments were performed at 4° C. or on ice.

(1-2) Binding Experiments

Invention of this Application

Lysate-binding experiments were performed per the procedures shown below using the FK506-bound affinity resin synthesized in Production Example 3 and the stearic-acid-immobilized resin prepared in Production Example 4. Note that the lysate was used after being diluted with the mixture A at a dilution rate of ½.

Each resin (10 μl) and the lysate (1 ml) were gently shaken at 4° C. for about 1 hour. Thereafter, centrifugal operation was performed, and each supernatant was collected carefully. Then, each supernatant was again mixed with a fresh supply of the FK506-bound resin (10 μl). After the mixture was gently stirred for about 3 hours, centrifugal operation was performed, and the supernatant was removed. The FK506-bound resin obtained was gently washed with the mixture A about 5 times to remove substances other than the protein bound onto the resin to the maximum possible extent.

To each FK506-bound resin thus obtained, 25 μl of a loading buffer for SDS (nakalai cat. NO=30566-22, sample buffer solution for electrophoresis with 2-ME (2-mercaptoethanol) (2×) for SDS PAGE) was added; this was followed by stirring at 25° C. for 10 minutes. The sample solution thus obtained was separated using a commercially available SDS gel (Bio-Rad readyGel J, 15% SDS, cat. NO=161-J341), and the SDS gel was analyzed.

As a result, compared to the first resin treatment performed with the stearic-acid-immobilized resin, the treatment with the FK506-bound resin showed that the band of FKBP12, which is considered to specifically bind onto the FK506-bound resin, decreased evidently and antagonism was observed.

Note that this result was very similar to the result from ordinary experiments (conventional method) described below.

(1-3) Binding Experiments

Conventional Method

Binding experiments were performed by a conventional method using the FK506-bound affinity resin synthesized in Production Example 3. Note that the same lysate as prepared in Example 2 was used in divided portions.

Two portions of the FK506-bound affinity resin synthesized in Production Example 3 (10 μl, FK506 content about 0.24 μmol) were provided; one portion was mixed with lysate (1 ml), 10 μl of DMSO was added (to ensure the same conditions as the experiments described below), and the mixture was gently shaken at 4° C. for about 1 hour. The lysate used for the other portion was obtained by adding 10 μl (0.35 μmol, about 1.5 times the amount of ligand on the resin) of a solution of FK506 (2.83 mg) dissolved in 100 μl of DMSO in advance before mixing with the resin, and gently stirring the solution for 1 hour. Note that a prior survey had confirmed that the addition of these amounts of DMSO and FK506 did not cause protein denaturation or aggregation like those described above. After each mixture was gently stirred for about 3 hours, centrifugal operation was performed, and the supernatant was removed. The FK506-bound resin obtained was washed carefully with the mixture A about 5 times to remove substances other than the protein bound onto the resin to the maximum possible extent.

To each FK506-bound resin thus obtained, 25 μl of a loading buffer for SDS (nakalai cat. NO=30566-22, sample buffer solution for electrophoresis with 2-ME (2-mercaptoethanol) (2×) for SDS PAGE) was added, and this was followed by stirring at 25° C. for 10 minutes. The sample solution thus obtained was separated using a commercially available SDS gel (BioRad readyGel J, 15% SDS, cat. NO=161-J341), and the SDS gel was analyzed.

As a result, the band of FKBP12, which is considered to specifically bind onto the resin, disappeared when the antagonist FK506 was added in advance, and antagonism was observed.

(1-4) Binding Experiments

Invention of this Application

Note that the same results as "(1-2) Binding experiments" above can also be obtained with the procedures shown below.

Lysate-binding experiments were performed using the FK506-bound affinity resin synthesized in Production Example 3 per the procedures shown below. Note that the lysate was used after being diluted with the mixture A at a dilution rate of ½.

The resin (10 μl) and the lysate (1 ml) were gently shaken at 4° C. for about 1 hour. Thereafter, centrifugal operation was performed, and each supernatant was collected carefully. At this time, the separated FK506-bound resin was kept to stand at 4° C. as the first binding experiment resin. Then, each supernatant was again mixed with a fresh supply of the FK506-bound resin (10 μl). After the mixture was gently stirred for about 3 hours, centrifugal operation was performed, and the supernatant was removed. Subsequently, the FK506-bound resin obtained in the second binding experiment and the resin obtained in the first binding experiment were gently washed with the mixture A about 5 times to remove substances other than the protein bound onto the resin to the maximum possible extent. To each FK506-bound resin thus obtained, 25 μl of a loading buffer for SDS (nakalai cat. NO=30566-22, sample buffer solution for electrophoresis with 2-ME (2-mercaptoethanol) (2×) for SDS PAGE) was added, and this was followed by stirring at 25° C. for 10 minutes. The sample solution thus obtained was separated using a commercially available SDS gel (BioRad readyGel J, 15% SDS, cat. NO=161-J341), and the SDS gel was analyzed.

Figure 3:
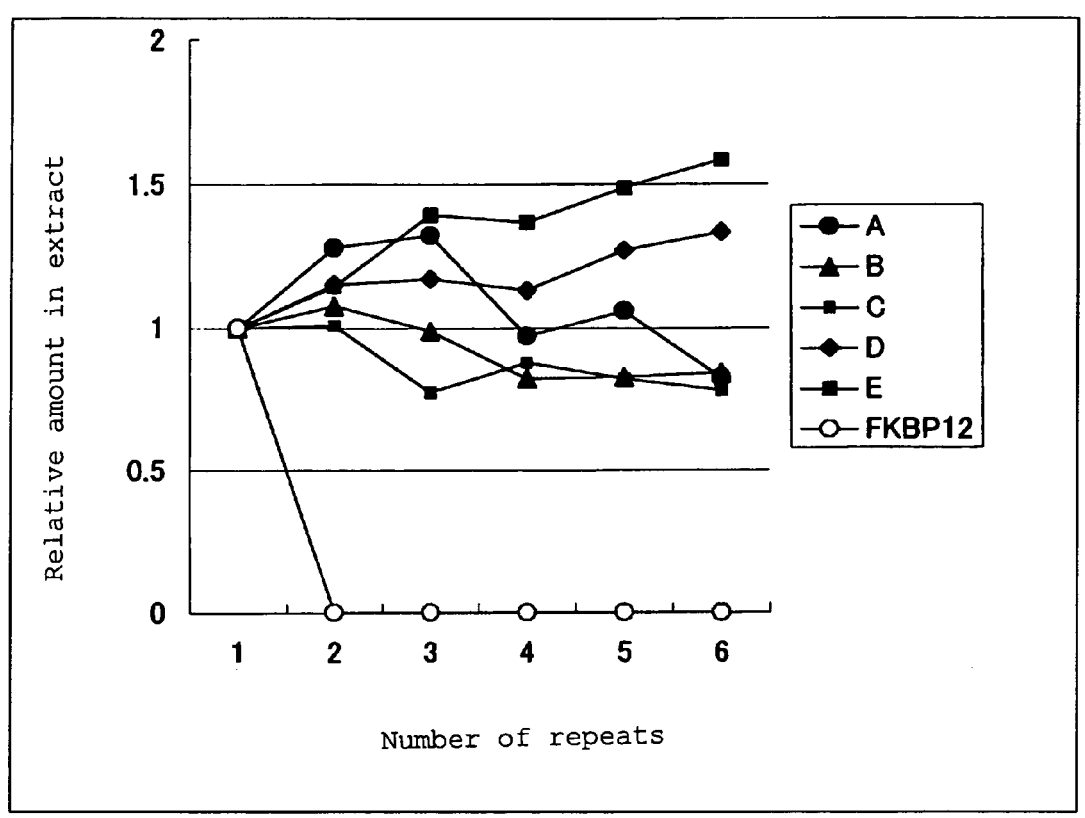
FIG. 3 is a drawing showing that the binding of a molecule capable of binding to a ligand is specific (ligand: FK506). In the figure, A to E are the results for optionally chosen proteins that were expected not to be specific for FK506.

As a result, on the resin obtained in the first binding experiment, nearly the same results as the results from the stearic-acid-immobilized resin treatment in "(1-2) Binding experiments" above were obtained, and from the resin obtained in the second binding experiment, nearly the same results as the results from the FK506-bound resin treatment in "(1-2) Binding experiments" above were obtained. Note that these results were very similar to the results described in "(1-2) Binding experiments (invention of this application)" and "(1-3) Binding experiments (conventional method)" above. The results from a total of up to six repeats of the procedure described in (1-4) are shown in FIG. 3. As shown in FIG. 3, a band of FKBP12, which is known to specifically bind to FK506, which was used as the ligand, was present only after the first operation and not at all present after the second operation and beyond. Also, the binding amounts of other proteins considered to be non-specific proteins, such as tubulin and actin, were nearly constant irrespective of the number of repeats of the operation. In target search using an affinity resin, antagonism experiments play an important role in confirming determining the specificity of the bands observed. The invention of this application provides one technique for antagonism experiments, which is free of the problem of the solubility of subject ligand, that has conventionally been a matter of concern, and which is associated with less problems of the non-specific protein denaturing effect by the subject ligand to be added. This technique is considered to serve as a basic technology for research into affinity resins.

Preferred embodiments of this invention are described herein, including the best mode known to the inventors for carrying out the invention. It should be understood that the illustrated embodiments are exemplary only, and should not be taken as limiting the scope of the invention. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

The invention claimed is:

1. A method of determining whether or not the binding of a target molecule to a ligand is specific, the method comprises:
   (i) dividing a sample containing the target molecule into first and second portions, and treating the first portion with a solid phase carrier comprising an immobilized inert substance to obtain a first once-treated liquid,
   (ii) treating the first once-treated liquid with a solid phase carrier comprising an immobilized ligand that binds the target molecule to obtain a first twice-treated liquid,
   (iii) extracting the target molecule bound to the ligand immobilized on the solid phase carrier in (ii) to obtain a first extract,
   (iv) treating the second portion with a solid phase carrier comprising the immobilized ligand as in step (ii) that binds the target molecule to obtain a second once-treated liquid,
   (v) treating the second once-treated liquid with a solid phase carrier comprising the immobilized ligand as in step (iv) that binds the target molecule to obtain a second twice-treated liquid,
   (vi) extracting the target molecule bound to the ligand immobilized on the solid phase carrier in (v) to obtain a second extract,
   (vii) comparing and/or analyzing the target molecule contained in the ligand-immobilized solid phase carrier first extract and the target molecule contained in the ligand-immobilized solid phase carrier second extract, and
   (viii) identifying the target molecule as being specific for the ligand if the target molecule is detected in the ligand-immobilized solid phase carrier first extract and not detected in the ligand-immobilized solid phase carrier second extract, or detected in the ligand-immobilized solid phase carrier second extract at a significantly lower level than in the ligand-immobilized solid phase carrier first extract.

2. The method of claim 1, wherein the inert substance is stearic acid.

3. The method of claim 1, wherein the inert substance is structurally similar to the ligand, has non-specific absorption and does not possess the physiological activity possessed by the ligand.

4. The method of claim 1, wherein the sample is a biological sample.

5. The method of claim 1, which further comprises calculating the binding constant of the target molecule binding to the ligand.

* * * * *